United States Patent
Rotem et al.

(10) Patent No.: US 9,056,160 B2
(45) Date of Patent: *Jun. 16, 2015

(54) MAGNETICALLY BALANCED FINGER-TYPE PERISTALTIC PUMP

(71) Applicant: Q-CORE MEDICAL LTD., Netanya (IL)

(72) Inventors: Shachar Rotem, M.P. Hefer (IL); Ori Goldor, Amikam (IL)

(73) Assignee: Q-CORE MEDICAL LTD, Netanya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/016,105

(22) Filed: Sep. 1, 2013

(65) Prior Publication Data

US 2014/0005631 A1      Jan. 2, 2014

Related U.S. Application Data

(63) Continuation of application No. 12/463,399, filed on May 10, 2009, now Pat. No. 8,535,025, which is a continuation-in-part of application No. PCT/IL2007/001400, filed on Nov. 13, 2007, and a continuation-in-part of application No. PCT/IL2007/001402, filed on Nov. 13, 2007.

(30) Foreign Application Priority Data

Nov. 13, 2006  (IL) .......................... 179229
Nov. 13, 2006  (IL) .......................... 179232

(51) Int. Cl.
F04B 43/09     (2006.01)
F04B 43/12     (2006.01)
(Continued)

(52) U.S. Cl.
CPC .......... *A61M 5/14228* (2013.01); *F04B 43/082* (2013.01)

(58) Field of Classification Search
CPC ..................... F04B 43/082; A61M 5/14228
USPC ........................................ 417/477.1, 374, 474
See application file for complete search history.

(56) References Cited

U.S. PATENT DOCUMENTS 2,056,322 A    10/1936  Hoppe
2,743,898 A     5/1956  King
(Continued)

FOREIGN PATENT DOCUMENTS

DE    10118086 A1    7/2002
EP     0215249 A1    3/1987
(Continued)

OTHER PUBLICATIONS

Honeywell Sensing and Control, "FSSI500NSB force sensor", Golden Valley, Minnesota, USA, 1998-2004 http://sccatalog.honeywell.com/imc/printfriendly.asp?FAM~force&PN-FSSI500NSB (5 pages).

(Continued)

*Primary Examiner* — Alexander Comley
(74) *Attorney, Agent, or Firm* — Vladimir Sherman; Professional Patent Solutions

(57) ABSTRACT

A peristaltic pump includes a plurality of effecters, actuated in a periodic manner upon by obstructive forces of a flexible infusion tube so as flow of infusion fluid is provided along said infusion tube, the magnitude of the obstructive forces being dependent upon the displacement of said moving effecters; and a plurality of balancing magnets providing balancing forces upon one or all the moving effecters, the balancing forces at each point along the path of motion of the moving effecters being of approximately equal magnitude to that of the obstructive forces at the point; such that the parasitic output due to work performed against the obstructive forces is approximately zero and yield is maximized.

14 Claims, 6 Drawing Sheets

(51) Int. Cl.
  *F04B 45/067* (2006.01)
  *F04B 45/08* (2006.01)
  *A61M 5/142* (2006.01)
  *F04B 43/08* (2006.01)

(56) References Cited

U.S. PATENT DOCUMENTS

| | | | |
|---|---|---|---|
| 2,981,115 A * | 4/1961 | Beguin | 74/25 |
| 3,443,585 A | 5/1969 | Reinicke | |
| 3,511,583 A * | 5/1970 | Brown | 417/412 |
| 3,677,667 A * | 7/1972 | Morrison | 417/474 |
| 3,778,195 A | 12/1973 | Bamberg | |
| 3,982,722 A * | 9/1976 | Bernard | 251/4 |
| 3,982,725 A | 9/1976 | Clark | |
| 4,014,318 A * | 3/1977 | Dockum et al. | 600/16 |
| 4,039,269 A | 8/1977 | Pickering | |
| 4,155,362 A | 5/1979 | Jess | |
| 4,178,138 A | 12/1979 | Iles | |
| 4,236,880 A | 12/1980 | Archibald | |
| 4,270,532 A | 6/1981 | Franetzki et al. | |
| 4,290,346 A | 9/1981 | Bujan | |
| 4,320,781 A | 3/1982 | Bouvet et al. | |
| 4,373,525 A * | 2/1983 | Kobayashi | 417/63 |
| 4,450,375 A | 5/1984 | Siegal | |
| 4,479,797 A | 10/1984 | Kobayashi et al. | |
| 4,489,863 A | 12/1984 | Horchos et al. | |
| 4,493,706 A | 1/1985 | Borsanyi et al. | |
| 4,682,135 A | 7/1987 | Yamakawa | |
| 4,690,673 A * | 9/1987 | Bloomquist | 604/67 |
| 4,725,205 A | 2/1988 | Cannon et al. | |
| 4,728,265 A * | 3/1988 | Cannon | 417/363 |
| 4,741,736 A | 5/1988 | Brown | |
| 4,748,003 A | 5/1988 | Riley | |
| 4,755,168 A | 7/1988 | Romanelli et al. | |
| 4,836,752 A * | 6/1989 | Burkett | 417/12 |
| 4,867,744 A | 9/1989 | Borsanyi | |
| 4,893,991 A * | 1/1990 | Heminway et al. | 417/53 |
| 4,978,335 A | 12/1990 | Arthur, III | |
| 5,074,756 A | 12/1991 | Davis | |
| 5,078,683 A | 1/1992 | Sancoff et al. | |
| 5,096,385 A | 3/1992 | Georgi et al. | |
| 5,103,211 A | 4/1992 | Daoud et al. | |
| 5,151,019 A | 9/1992 | Danby et al. | |
| 5,152,680 A | 10/1992 | Okada | |
| 5,165,874 A | 11/1992 | Sancoff et al. | |
| 5,213,483 A | 5/1993 | Flaherty et al. | |
| 5,219,327 A | 6/1993 | Okada | |
| 5,222,946 A | 6/1993 | Kamen | |
| 5,246,347 A | 9/1993 | Davis | |
| 5,257,978 A | 11/1993 | Haber et al. | |
| 5,286,176 A * | 2/1994 | Bonin | 417/413.1 |
| 5,290,158 A | 3/1994 | Okada | |
| 5,338,157 A | 8/1994 | Blomquist | |
| 5,395,320 A | 3/1995 | Padda et al. | |
| 5,429,485 A | 7/1995 | Dodge | |
| 5,485,408 A | 1/1996 | Blomquist | |
| 5,499,969 A | 3/1996 | Beuchat et al. | |
| 5,509,439 A | 4/1996 | Tantardini | |
| 5,527,295 A | 6/1996 | Wing | |
| 5,569,188 A | 10/1996 | Mackool | |
| 5,575,309 A | 11/1996 | Connell | |
| 5,575,631 A | 11/1996 | Jester | |
| 5,577,891 A | 11/1996 | Loughnane et al. | |
| 5,584,667 A | 12/1996 | Davis | |
| 5,593,134 A | 1/1997 | Steber et al. | |
| 5,601,420 A | 2/1997 | Warner et al. | |
| 5,628,619 A | 5/1997 | Wilson | |
| 5,658,250 A | 8/1997 | Blomquist et al. | |
| 5,658,252 A | 8/1997 | Johnson | |
| 5,660,529 A | 8/1997 | Hill | |
| 5,669,877 A | 9/1997 | Blomquist | |
| 5,683,233 A * | 11/1997 | Moubayed et al. | 417/474 |
| 5,695,473 A | 12/1997 | Olsen | |
| 5,704,584 A | 1/1998 | Winterer et al. | |
| 5,782,805 A | 7/1998 | Meinzer et al. | |
| 5,788,669 A | 8/1998 | Peterson | |
| 5,791,880 A | 8/1998 | Wilson | |
| 5,791,881 A | 8/1998 | Moubayed et al. | |
| 5,803,712 A | 9/1998 | Davis et al. | |
| 5,807,322 A | 9/1998 | Lindsey et al. | |
| 5,810,323 A | 9/1998 | Winterer et al. | |
| 5,853,386 A | 12/1998 | Davis et al. | |
| 5,876,370 A | 3/1999 | Blomquist | |
| 5,888,052 A * | 3/1999 | Hill | 417/53 |
| 5,896,076 A * | 4/1999 | van Namen | 335/229 |
| 5,909,724 A | 6/1999 | Nishimura et al. | |
| 5,924,852 A | 7/1999 | Moubayed et al. | |
| 5,935,099 A | 8/1999 | Peterson et al. | |
| 5,935,106 A | 8/1999 | Olsen | |
| 5,954,485 A | 9/1999 | Johnson et al. | |
| 5,980,490 A | 11/1999 | Tsoukalis | |
| 5,996,964 A * | 12/1999 | Ben-Shalom | 251/4 |
| 6,024,539 A | 2/2000 | Blomquist | |
| 6,095,189 A | 8/2000 | Ben-Shalom | |
| 6,110,153 A | 8/2000 | Davis et al. | |
| 6,146,109 A | 11/2000 | Davis et al. | |
| 6,164,921 A | 12/2000 | Moubayed et al. | |
| 6,165,874 A | 12/2000 | Powell et al. | |
| RE37,074 E | 2/2001 | Danby et al. | |
| 6,203,296 B1 | 3/2001 | Ray et al. | |
| 6,213,723 B1 | 4/2001 | Danby et al. | |
| 6,213,739 B1 | 4/2001 | Phallen et al. | |
| 6,234,773 B1 | 5/2001 | Hill et al. | |
| 6,241,704 B1 | 6/2001 | Peterson et al. | |
| 6,261,262 B1 | 7/2001 | Briggs et al. | |
| 6,312,227 B1 | 11/2001 | Davis | |
| 6,339,410 B1 | 1/2002 | Milner et al. | |
| 6,347,553 B1 | 2/2002 | Morris et al. | |
| 6,371,732 B1 * | 4/2002 | Moubayed et al. | 417/44.1 |
| 6,450,773 B1 | 9/2002 | Upton | |
| 6,475,180 B2 | 11/2002 | Peterson et al. | |
| 6,519,569 B1 | 2/2003 | White et al. | |
| 6,537,244 B2 | 3/2003 | Paukovits et al. | |
| 6,558,347 B1 | 5/2003 | Jhuboo et al. | |
| 6,572,604 B1 | 6/2003 | Platt et al. | |
| 6,622,542 B2 | 9/2003 | Derek et al. | |
| 6,648,861 B2 | 11/2003 | Platt et al. | |
| 6,692,241 B2 * | 2/2004 | Watanabe et al. | 417/477.2 |
| 6,733,476 B2 | 5/2004 | Christenson et al. | |
| 6,742,992 B2 | 6/2004 | Davis | |
| 6,749,587 B2 | 6/2004 | Flaherty | |
| 6,768,425 B2 | 7/2004 | Flaherty et al. | |
| 6,788,199 B2 | 9/2004 | Crabtree et al. | |
| 6,790,198 B1 | 9/2004 | White et al. | |
| 6,902,549 B2 * | 6/2005 | Marmaropoulos et al. | 604/289 |
| 6,942,473 B2 | 9/2005 | Abrahamson et al. | |
| 7,018,361 B2 | 3/2006 | Gillespie, Jr. et al. | |
| 7,022,075 B2 | 4/2006 | Grunwald et al. | |
| 7,059,840 B2 | 6/2006 | Corwin et al. | |
| 7,122,026 B2 | 10/2006 | Rogers et al. | |
| 7,163,385 B2 | 1/2007 | Gharib et al. | |
| 7,347,836 B2 | 3/2008 | Peterson et al. | |
| 7,525,432 B2 | 4/2009 | Jackson | |
| 7,556,481 B2 | 7/2009 | Moubayed | |
| 7,645,258 B2 | 1/2010 | White et al. | |
| 7,654,976 B2 | 2/2010 | Peterson et al. | |
| 7,695,255 B2 | 4/2010 | Ben-Shalom et al. | |
| 7,698,156 B2 | 4/2010 | Martucci et al. | |
| 7,704,227 B2 | 4/2010 | Moberg et al. | |
| 7,762,795 B2 | 7/2010 | Moubayed | |
| 7,840,260 B2 | 11/2010 | Epley | |
| 7,892,332 B2 | 2/2011 | Prisco et al. | |
| 7,938,796 B2 | 5/2011 | Moubayed et al. | |
| 7,963,946 B2 | 6/2011 | Moubayed et al. | |
| 7,998,121 B2 | 8/2011 | Stringham | |
| 8,025,634 B1 | 9/2011 | Moubayed et al. | |
| 8,029,253 B2 | 10/2011 | Rotem et al. | |
| 8,142,400 B2 | 3/2012 | Rotem et al. | |
| 8,182,445 B2 | 5/2012 | Moubayed et al. | |
| 8,197,235 B2 | 6/2012 | Davis | |
| 8,214,231 B2 | 7/2012 | Martucci et al. | |
| 8,234,128 B2 | 7/2012 | Martucci et al. | |
| 8,241,018 B2 | 8/2012 | Harr | |
| 8,308,457 B2 | 11/2012 | Rotem et al. | |

(56) References Cited

U.S. PATENT DOCUMENTS

| | | | |
|---|---|---|---|
| 8,337,168 | B2 | 12/2012 | Rotem et al. |
| 8,343,111 | B2 | 1/2013 | Beck et al. |
| 8,352,290 | B2 | 1/2013 | Bartz et al. |
| 8,371,832 | B2 * | 2/2013 | Rotem et al. ............... 417/477.7 |
| 8,489,427 | B2 | 7/2013 | Simpson et al. |
| 8,535,025 | B2 * | 9/2013 | Rotem et al. ............... 417/477.1 |
| 8,672,875 | B2 | 3/2014 | Vanderveen et al. |
| 8,678,793 | B2 | 3/2014 | Goldor et al. |
| 2001/0029321 | A1 | 10/2001 | Beetz et al. |
| 2002/0094287 | A1 | 7/2002 | Davis |
| 2002/0156402 | A1 | 10/2002 | Woog et al. |
| 2002/0165503 | A1 | 11/2002 | Morris et al. |
| 2003/0034887 | A1 | 2/2003 | Crabtree et al. |
| 2003/0040700 | A1 | 2/2003 | Hickle et al. |
| 2003/0065536 | A1 | 4/2003 | Hansen et al. |
| 2003/0109988 | A1 | 6/2003 | Geissler et al. |
| 2003/0140928 | A1 | 7/2003 | Bui et al. |
| 2003/0141981 | A1 | 7/2003 | Bui et al. |
| 2003/0182586 | A1 | 9/2003 | Numano |
| 2004/0167804 | A1 | 8/2004 | Simpson et al. |
| 2004/0172222 | A1 | 9/2004 | Simpson et al. |
| 2004/0181314 | A1 | 9/2004 | Zaleski |
| 2004/0191112 | A1 | 9/2004 | Hill et al. |
| 2004/0204673 | A1 | 10/2004 | Flaherty |
| 2004/0204685 | A1 | 10/2004 | Wright et al. |
| 2004/0235446 | A1 | 11/2004 | Flaherty et al. |
| 2005/0001369 | A1 | 1/2005 | Cross |
| 2005/0022274 | A1 | 1/2005 | Campbell et al. |
| 2005/0055242 | A1 | 3/2005 | Bello et al. |
| 2005/0088409 | A1 | 4/2005 | Van Berkel |
| 2005/0112001 | A1 | 5/2005 | Bahnen et al. |
| 2005/0171501 | A1 | 8/2005 | Kelly |
| 2005/0191196 | A1 | 9/2005 | Tanner et al. |
| 2005/0214146 | A1 | 9/2005 | Corwin et al. |
| 2006/0051218 | A1 | 3/2006 | Harttig |
| 2006/0083644 | A1 | 4/2006 | Zumbrum et al. |
| 2006/0173419 | A1 | 8/2006 | Malcolm |
| 2007/0048161 | A1 | 3/2007 | Moubayed |
| 2007/0060872 | A1 | 3/2007 | Hall et al. |
| 2007/0118405 | A1 | 5/2007 | Campbell et al. |
| 2007/0135866 | A1 | 6/2007 | Baker et al. |
| 2007/0154336 | A1 | 7/2007 | Miyazaki et al. |
| 2007/0217931 | A1 * | 9/2007 | Estes et al. ............... 417/474 |
| 2007/0269324 | A1 | 11/2007 | Goldor et al. |
| 2008/0015506 | A1 | 1/2008 | Davis |
| 2008/0065007 | A1 | 3/2008 | Peterson et al. |
| 2008/0065016 | A1 | 3/2008 | Peterson et al. |
| 2008/0067462 | A1 | 3/2008 | Miller et al. |
| 2008/0071251 | A1 | 3/2008 | Moubayed et al. |
| 2008/0095649 | A1 * | 4/2008 | Ben-Shalom et al. ........ 417/474 |
| 2008/0145249 | A1 | 6/2008 | Smisson et al. |
| 2008/0146995 | A1 | 6/2008 | Smisson et al. |
| 2009/0088675 | A1 | 4/2009 | Kelly et al. |
| 2009/0163864 | A1 | 6/2009 | Breznock et al. |
| 2009/0203329 | A1 | 8/2009 | White et al. |
| 2009/0221964 | A1 | 9/2009 | Rotem et al. |
| 2009/0240201 | A1 | 9/2009 | Rotem et al. |
| 2009/0300507 | A1 | 12/2009 | Raghavan et al. |
| 2009/0317268 | A1 | 12/2009 | Rotem et al. |
| 2010/0016781 | A1 | 1/2010 | Nakayama et al. |
| 2010/0036322 | A1 | 2/2010 | Rotem |
| 2010/0082001 | A1 | 4/2010 | Beck et al. |
| 2010/0168545 | A1 | 7/2010 | Kamath et al. |
| 2010/0211002 | A1 | 8/2010 | Davis |
| 2010/0228223 | A1 | 9/2010 | Williams et al. |
| 2010/0279652 | A1 | 11/2010 | Sharp et al. |
| 2011/0152772 | A1 | 6/2011 | Rotem et al. |
| 2011/0152831 | A1 | 6/2011 | Rotem et al. |
| 2011/0264043 | A1 | 10/2011 | Kotnik et al. |
| 2011/0276000 | A1 | 11/2011 | Stringham |
| 2011/0318208 | A1 | 12/2011 | Goldor et al. |
| 2012/0062387 | A1 | 3/2012 | Vik et al. |
| 2012/0241525 | A1 | 9/2012 | Borges et al. |
| 2013/0006666 | A1 | 1/2013 | Schneider et al. |
| 2013/0116620 | A1 | 5/2013 | Rotem et al. |
| 2013/0116623 | A1 | 5/2013 | Rotem et al. |
| 2013/0142670 | A1 * | 6/2013 | Rotem et al. ............... 417/53 |
| 2013/0209275 | A1 | 8/2013 | Rotem et al. |
| 2013/0279370 | A1 | 10/2013 | Eitan et al. |
| 2014/0005631 | A1 | 1/2014 | Rotem et al. |
| 2014/0119954 | A1 | 5/2014 | Schweitzer et al. |
| 2014/0197824 | A1 | 7/2014 | Gillespie et al. |
| 2014/0222377 | A1 | 8/2014 | Bitan et al. |
| 2014/0276564 | A1 | 9/2014 | Schneider |

FOREIGN PATENT DOCUMENTS

| | | | |
|---|---|---|---|
| EP | 0225158 | A2 | 6/1987 |
| EP | 0315312 | A1 | 5/1989 |
| EP | 0429866 | A1 | 6/1991 |
| EP | 0483794 | A1 | 5/1992 |
| EP | 0858812 | A2 | 8/1998 |
| EP | 1031358 | A1 | 8/2000 |
| EP | 1350955 | A2 | 10/2003 |
| EP | 1557186 | | 7/2005 |
| EP | 1611834 | A2 | 1/2006 |
| EP | 1485149 | B1 | 7/2008 |
| FR | 2632529 | A1 | 12/1989 |
| FR | 2753236 | A1 | 3/1998 |
| JP | 60043188 | A | 3/1985 |
| JP | 6-169992 | A | 6/1994 |
| JP | 2002-57738 | A | 2/2002 |
| JP | 2004141418 | A | 5/2004 |
| WO | 8400691 | A1 | 3/1984 |
| WO | 9116933 | A1 | 11/1991 |
| WO | 9325816 | A1 | 12/1993 |
| WO | 9408647 | A1 | 4/1994 |
| WO | 9603168 | A1 | 2/1996 |
| WO | 9630679 | A1 | 10/1996 |
| WO | 9734084 | A1 | 9/1997 |
| WO | 9804301 | A1 | 2/1998 |
| WO | 9813080 | A2 | 4/1998 |
| WO | 9847551 | A1 | 10/1998 |
| WO | 0139816 | A2 | 6/2001 |
| WO | 0165232 | A1 | 9/2001 |
| WO | 0236044 | A2 | 5/2002 |
| WO | 0238204 | A2 | 5/2002 |
| WO | 0249509 | A2 | 6/2002 |
| WO | 0268015 | A2 | 9/2002 |
| WO | 03027503 | A1 | 4/2003 |
| WO | 03080158 | A1 | 10/2003 |
| WO | 2004070548 | A2 | 8/2004 |
| WO | 2004093648 | A2 | 11/2004 |
| WO | 2005089263 | A2 | 9/2005 |
| WO | 2007133259 | A1 | 11/2007 |
| WO | 2008036658 | A2 | 3/2008 |
| WO | 2008059492 | A2 | 5/2008 |
| WO | 2008059493 | A2 | 5/2008 |
| WO | 2008059494 | A2 | 5/2008 |
| WO | 2008059495 | A2 | 5/2008 |
| WO | 2008059496 | A2 | 5/2008 |
| WO | 2008059498 | A2 | 5/2008 |
| WO | 2008059499 | A2 | 5/2008 |
| WO | 2008130644 | A1 | 10/2008 |
| WO | 2010053702 | A1 | 5/2010 |
| WO | 2010053703 | A1 | 5/2010 |
| WO | 2010091313 | A2 | 8/2010 |
| WO | 2011128850 | A2 | 10/2011 |
| WO | 2012095827 | A1 | 7/2012 |
| WO | 2012095829 | A2 | 7/2012 |
| WO | 2013001425 | A2 | 1/2013 |

OTHER PUBLICATIONS

International Application PCT/IL2007/001398 Search Report dated Jun. 11, 2008 (2 pages).
International Application PCT/IL2007/001398 Patentability Report dated May 19, 2009 (6 pages).
International Application PCT/IL2007/001399 Search Report dated Jun. 4, 2008 (3 pages).
International Application PCT/IL2007/001399 Patentability Report dated May 19, 2009 (9 pages).
International Application PCT/IL2007/001400 Search Report dated Jul. 15, 2008 (3 pages).

(56) References Cited

OTHER PUBLICATIONS

International Application PCT/IL2007/001400 Patentability Report dated May 19, 2009 (10 pages).
International Application PCT/IL2007/001401 Search Report dated Sep. 24, 2008 (2 pages).
International Application PCT/IL2007/001401 Patentability Report dated May 19, 2009 (11 pages).
International Application PCT/IL2007/001402 Search Report dated Jun. 20, 2008 (3 pages).
International Application PCT/IL2007/001402 Patentability Report dated May 19, 2009 (4 pages).
International Application PCT/IL2007/001404 Search Report dated Jul. 14, 2008 (2 pages).
International Application PCT/IL2007/001404 Patentability Report dated May 19, 2009 (7 pages).
International Application PCT/IL2007/001405 Search Report dated Jul. 21, 2008 (4 pages).
International Application PCT/IL2007/001405 Patentability Report dated May 19, 2009 (7 pages).
International Application PCT/IL2005/001249 Search Report dated Apr. 5, 2006 (18 pages).
International Application PCT/IL1997/000289 Search report dated Jan. 27, 1998 (18 pages).
International Application PCT/IL1997/000290 Search Report dated Jan. 27, 1998 (18 pages).
International Application PCT/IL2003/000947 Search Report dated Mar. 3, 2004 (43 pages).
International Application PCT/IB2011/051586 Search Report dated Oct. 27, 2011 (3 pages).
International Application PCT/IB2011/051586 Patentability Report dated Oct. 16, 2012 (9 pages).
International Application PCT/IB2012/050192 Search Report dated Aug. 17, 2012 (2 pages).
International Application PCT/IB2012/050192 Patentability Report dated Jul. 16, 2013 (6 pages).
International Application PCT/IB2012/050189 Search Report dated May 30, 2012 (2 pages).
International Application PCT/IB2012/050189 Patentability Report dated Jul. 16, 2013 (5 pages).
International Application PCT/IB2012/053149 Search Report dated Jan. 15, 2013 (2 pages).
U.S. Appl. No. 09/125,438 Official Action dated May 3, 1999 (4 pages).
U.S. Appl. No. 09/125,438 Official Action dated Jul. 15, 1999 (7 pages).
U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance issued Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).
U.S. Appl. No. 13/229,798 Notice of Allowance issued Apr. 19, 2013 (6 pages).
U.S. Appl. No. 13/229,798 Notice of Withdrawal from Issue dated May 13, 2013 (1 page).
U.S. Appl. No. 13/229,798 Official Action (Non-Final) dated Jun. 21, 2013 (6 pages).
Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, issued Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).
U.S. Appl. No. 12/464,202 Notice of Allowance issued Jul. 11, 2012 (5 pages).
U.S. Appl. No. 12/463,399 Official Action (Non-Final) dated Jul. 21, 2011 (15 pages).
U.S. Appl. No. 12/463,399 Response to Official Action (Non-Final) dated Jul. 21, 2011, submitted Oct. 21, 2011 (5 pages).
U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance issued Apr. 29, 2013 (14 pages).
U.S. Appl. No. 12/514,310 Official Action (Non-Final) dated Jul. 21, 2011 (8 pages).
U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance issued Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011 (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.
U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance issued Oct. 11, 2012 (10 pages).

(56) References Cited

OTHER PUBLICATIONS

U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance issued Nov. 17, 2011 (5 pages).
U.S. Appl. No. 13/229,798 Response to Official Action (Non-Final) dated Jun. 21, 2013, submitted Oct. 21, 2013 (3 pages).
U.S. Appl. No. 13/229,798 Notice of Allowance issued Nov. 14, 2013 (54 pages).
U.S. Appl. No. 13/651,420 Official Action (Non-Final) dated Nov. 4, 2013 (8 pages).
U.S. Appl. No. 13/651,420 Response to Official Action (Non-Final) dated Nov. 4, 2013, submitted Nov. 21, 2013 (2 pages).
U.S. Appl. No. 13/681,440 Official Action (Non-Final) dated Oct. 24, 2013 (11 pages).
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance issued Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).

\* cited by examiner

|          | Stage 1 | Stage 2 | Stage 3 | Stage 4 |                              |
|----------|---------|---------|---------|---------|------------------------------|
| Finger 4 |         |         |         |         | Tube loosened Tube compressed |
| Finger 3 |         |         |         |         | Tube loosened Tube compressed |
| Finger 2 |         |         |         |         | Tube loosened Tube compressed |
| Finger 1 |         |         |         |         | Tube loosened Tube compressed |
| Cycle    | T/4     | T/4     | T/4     | T/4     |                              |

*Fig. 3*

MAGNETICALLY BALANCED FINGER-TYPE PERISTALTIC PUMP

CROSS-REFERENCE TO RELATED APPLICATIONS

This application is a continuation of U.S. patent application Ser. No. 12/463,399, filed May 10, 2009 by the inventors of the present application and entitled "MAGNETICALLY BALANCED FINGER-TYPE PERISTALTIC PUMP";

U.S. application Ser. No. 12/463,399 is, in turn, a continuation-in-part of PCT International Application PCT/IL2007/001400 filed on Nov. 13, 2007 by the inventors of the present application;

U.S. application Ser. No. 12/463,399 is also a continuation-in-part of PCT International Application PCT/IL2007/001402, filed on Nov. 13, 2007 by the inventors of the present application;

International Application PCT/IL2007/001400 claims, in turn, priority from Israel Patent Application No. 179229, filed on Nov. 13, 2006; and International Application PCT/IL2007/001402 claims, in turn, priority from Israel Patent Application No. 179232, filed on Nov. 13, 2006;

all of the aforementioned applications are hereby incorporated herein by reference in their entirety.

FIELD OF THE INVENTION

The present invention generally relates to a magnetically balanced finger-type peristaltic pump, especially a pump comprising at least one tailor made cam.

BACKGROUND OF THE INVENTION

This invention relates to designs for cams to operate magnetically balanced fingers of a peristaltic pump. At present peristaltic pumps find use in medical settings to add nutrients to blood, to force blood through filters to clean it as in dialysis, or to move blood through the body and lungs during open heart surgery. They are advantageous in these situations since the pump elements do not contact the pumped fluid, eliminating any possibility of contamination. Additionally the pumping action may be gentle enough that blood cells are not damaged. Further uses include pumping aggressive chemicals, high solids slurries and other materials where isolation of the product from the environment, and the environment from the product, are critical. As the operation of such a pump can be critical for life support, they are generally provided with battery backup. The efficiency of the device thus becomes an important parameter since the length of time it can remain in operation while on battery power is limited by its efficiency.

A common arrangement for the operation of a peristaltic pump is shown in the prior art of FIG. 1 (100 is a front view and 101 is a lateral view), wherein a plurality of fingers 104 press the feed tube 103 against a substrate 105 by means of a cam 102. Neighboring fingers are operated in sequence such that a squeezing or 'peristaltic' motion operates along the length of the tube, forcing the contents of the tube in one direction. By adjusting the speed of rotation of the cams, the speed of pumping can be adjusted.

In U.S. Pat. No. 4,725,205 a mechanically compensated cam for use in a peristaltic pump is disclosed. The system described uses specially designed cams that reduce the maximum force applied between fingers 104 and tube 103 by means of a compliant spring. In this manner problems of jamming due to poor alignment or out-of-tolerance tubes are eliminated. This system while effective and simple involves a certain amount of wasted energy as will be described below. Furthermore, being based on an eccentric circle, the fingers follow a trajectory sinusoidal in nature, which limits the volume pumped per camshaft revolution. Varying the trajectory from that of a sinusoid would offer the benefit of fixing the duration during which the tube is shut off, allowing for an increase in the volume pumped per revolution.

Thus a design and method for the cam of a peristaltic pump allowing a tailored finger trajectory that reduces the probability of jamming in out-of-tolerance tubes, as well as allowing increased volume per rotation and subsequent enhanced energy savings is a long felt need.

BRIEF DESCRIPTION OF THE DRAWINGS

In order to understand the invention and to see how it may be implemented in practice, a plurality of embodiments will now be described, by way of non-limiting example only, with reference to the accompanying drawings, in which

FIG. 3 schematically presents the state of each finger at each of the four steps of a single pumping cycle wherein at each step, two fingers are static and two are moving;

SUMMARY OF THE INVENTION

Figure 1:
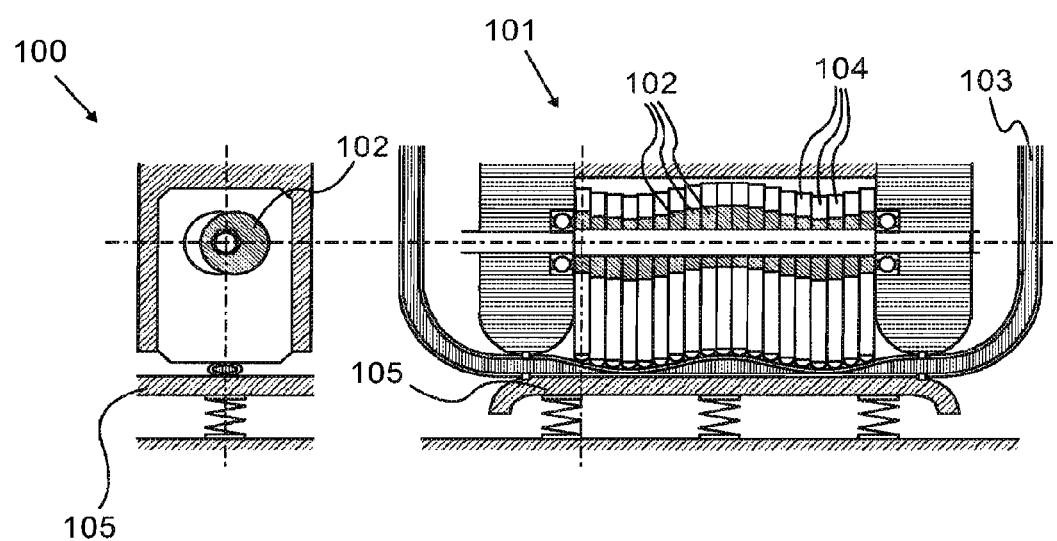
FIG. 1 shows in prior art a typical peristaltic pump making use of fingers 104 pressing against a uniform substrate 105.

In some embodiments a finger-type peristaltic pump (DDS) comprising a plurality of pressing-fingers, actuated in a periodic manner upon by obstructive forces of a flexible infusion tube so as peristaltic flow of infusion fluid is provided along said infusion tube, the magnitude of said obstructive forces being dependent upon the displacement of said moving finger; and a plurality of balancing magnets providing balancing forces upon said moving fingers, said balancing forces at each point along the path of motion of the moving member being of approximately equal magnitude to that of said obstructive forces at the point; such that the parasitic output due to work performed against said obstructive forces is approximately zero and yield is maximized.

A magnetically balanced finger-type peristaltic pump as defined above may be especially adapted to be utilized as ambulatory and hospital infusion pumps.

In some embodiments, a magnetically balanced finger-type peristaltic pump is defined as above wherein at least a portion of said plurality of pressing-fingers is magnetically balanced and wherein each of said magnetically balanced pressing-fingers comprises one or more magnets stacked in the direction of said pressing by means of one or more metal members, said metal member is optionally selected from ferromagnetic materials, fixed magnets, static magnets that are nor actuated in respect to the pressing-fingers or any combination thereof.

In some embodiments, the magnets are not located on the pressing fingers. Hence, at least a portion of the magnets are located in sides of the fingers, whereas iron or other magnetic materials are located on the fingers.

In some embodiments, a magnetically balanced finger-type peristaltic pump is defined as above, wherein each of said magnetically balanced pressing-fingers of linear movement is actuated periodically by a rotating cam towards a flexible infusion tube i.e., until a complete yet temporary shut off of said tube is obtained, and backwards, i.e., until said fingers are not pressing said tube; wherein said magnetic balance avoids significant pressing forces between said cam and said fingers.

In some embodiments, the pressing fingers maneuver along a non-linear movement, e.g., a curved movement etc.

In some embodiments, a magnetically balanced finger-type peristaltic pump is defined as above wherein said magnetic balance avoids significant pressing forces between said cam and said fingers along their entire forth and backwards linear movement. It is acknowledged in this respect that the force between the finger and the cam is negligible due to the balancing magnet force yielding almost no friction on the cam surface. As a result, no torque evolves on the cam and almost no energy is needed to rotate the pumping mechanism.

In some embodiments, a magnetically balanced finger-type peristaltic pump is defined as above wherein said fingers remain at maximum extension for a large angular sweep AO of the shaft, such as 87.5.degree., causing complete tube shutoff during said large and predetermined range.

In some embodiments, a magnetically balanced finger-type peristaltic pump is defined as above, comprising inter alia a plurality of N pressing fingers, N is any integer number higher 2, especially 4, wherein per any given pumping cycle, each of said fingers are in one of two alternating states of being either static or moving (or approaching to movement); in said static state said at least one finger is pressing said flexible infusion tube and at least one finger is withdrawn and not pressing said tube; in said moving state at least one finger is withdrawing from said tube and at least one finger is pressing the same.

In some embodiments, a magnetically balanced finger-type peristaltic pump is defined as above, wherein the static and moving states of said fingers per any given pumping cycle are as defined in FIG. 3.

In some embodiments a magnetically balanced finger-type peristaltic pump is defined as above, wherein at least a portion of said cams are characterized by one or more crescent forms, each of which of said crescent forms is adapted to provide pressing of said finger by magnetic forces of said balancing magnets in the manner that said magnetic forces are at least slightly stronger than the oppositely directed elastic forces, provided by the squeezing of said flexible tube by said finger while shutting off said tube; by applying said magnetic force, complete tube's shut off is assured, especially in cases of worn out tubes and pumping mechanisms with noticeable tolerances.

In some embodiments, a magnetically balanced finger-type peristaltic pump is defined as above wherein at least a portion of said cams are characterized by a first and a second crescent forms located in opposite directions: The first crescent form is adapted to provide pressing of said finger by magnetic forces of said balancing magnets in the manner that said magnetic forces are at least slightly stronger than the oppositely directed elastic forces, provided by the squeezing of said flexible tube by said finger while shutting off said tube; by applying said magnetic force, complete tube's shut off is assured. The second crescent form is adapted to provide additional finger movement in the direction of withdrawing said tube, so as complete tube's after-press inflation is assured, especially in cases of worn out tubes, wider tubes, tubes of wider walls, and pumping mechanisms with noticeable tolerances.

In some embodiments, a magnetically balanced finger-type peristaltic pump is defined as above wherein the pressing-finger are of rounded cross sections, additionally comprising sealing means that hermetically barriers between proximal portion of the fingers, i.e., the portion constantly located inside said pump's housing, and distal portion of said fingers, i.e., the pressing tip located outside said housing; said sealing means is especially selected from O-rings, U-rings or the like.

The magnetically balanced finger-type peristaltic pump as defined above is especially useful for reduce pumping energy and provide extended working time per given set of batteries. The system reduces mechanical wear of moving members, especially of cams and fingers. Less tube degradation is provided in the system. Scaling down is facilitated by reducing sizes of both engine and gear mechanism. Tube wear out is reduced, while improved accuracy is provided due to decrease degradation. The aforesaid pumping system also provides use of pumping mechanisms of bigger tolerances in production and assembly. The system provides for improved mechanical efficiency and allows use of sealed pressing-fingers so as sealed pump is obtained, and less sensitivity is obtained to dirt and contaminated body fluids. Lastly, the patented pumping system provides for downstream pressure built up without any requirements of applying high pumping moments.

In some embodiments, the peristaltic pump is defined as above, wherein at least a portion of said balancing magnets is located in a location selected from a group consisting of the elongated body portion of the finger-type pressing members (fingers), the fingers block or any combination thereof.

In some embodiments, the peristaltic pump is defined as above, wherein at least a portion of said balancing magnets comprises metal and other paramagnetic materials which location is one or more of a group consisting of in one or more portions of the finger-type pressing members (fingers), on one or more portions of the fingers, in the fingers block, on the fingers block or any combination thereof.

In some embodiments, at least a portion of said magnetically balanced pressing-fingers are actuated in at least partially non-linear movement.

In some embodiments, the magnetic force is applied in one or more specific points along the circumference of the rotating cam.

DETAILED DESCRIPTION OF PREFERRED EMBODIMENTS

The following description is provided so as to enable any person skilled in the art to make use of said invention and sets forth the best modes contemplated by the inventor of carrying out this invention. Various modifications, however, will remain apparent to those skilled in the art, and are considered to be within the scope of the present invention.

The terms 'about' or 'approximately' apply hereinafter to any value in a range from below 30% of a specified value to above 30% of said value.

The terms 'parasitic input' and 'parasitic output' apply hereinafter in the manner that parasitic input refers to the energy consumed by the system to produce parasitic output. The parasitic input is greater than the parasitic output because of internal losses. For example, an elevator with a cabin of weight 10,000 N being used to raise a man of weight 700 N through 10 m produces 107 kJ of output of which only 7 kJ are necessary output the remaining 100 kJ are parasitic output due to raising the cabin itself.

The term 'effecters' refers hereinafter to any portion of a device whose position changes during the working of the device, such as pressing fingers, peristaltic rollers etc.

The term 'necessary output' applies hereinafter to the energy needed to be produced by a system in order to perform the task for which the system is designed. For example in order perform the task of raising a man of weight 700 N through 10 m the necessary output of a system such as an elevator is 7 kJ of energy.

The term 'obstructive forces' refers hereinafter to any force which acts upon a moving member during its movement. More specifically this term is used to refer to forces dependent upon the displacement of a moving member.

The term 'output' applies hereinafter to energy produced by a system.

The term 'actuated in a periodic manner' applies hereinafter to any system wherein at least one component or effecter performs a series of steps repeatedly a plurality of times.

It is in the scope of the present invention to introduce the tailored cam, whose radius is not a circle rotating about an eccentric axis, but rather varies in such a manner that the fingers remain closed for a large sweep of the shaft, such as 87.5.degree. out of the full 360.degree. of rotation. The unique profile of the tailored cam allows complete tube shut-off during this large and predetermined range, preventing backflow through this entire range and allowing subsequent fingers a longer range of shaft angle .theta. in which to effect their peristaltic motion. This has an effect of decreasing the noise of the peristaltic pump, decreasing the energy consumption and effectively obtaining the conditions defined in the figures, e.g., FIG. 6.

It is furthermore within the scope of the present invention that a reduced-radius 'compliance zone' be included in the design of the cam, to accommodate tubes of increased diameter that would not otherwise be allowed to open completely. An out-of-compliance tube with increased diameter would remain partially closed even during the fingers' 'open' range but for the inclusion of the reduced radius 'compliance zone'. This partial closure would impede the free flow of fluid through the tube, reducing the throughput of the pump in such cases.

It is furthermore within the scope of the present invention and according to one specific embodiment of the same, wherein the aforementioned advantages are provided while still minimizing the first, second, and third derivatives of radius with shaft angle .theta The first derivative directly controls the finger velocity, and thus influences the kinetic energy invested therein. The second derivative affects the force upon the tube, which it is desirable to reduce insofar as possible in order to eliminate jamming, tube rupture, or disturbance of the fragile materials such as human cells passing through the tube. The third derivate controls the 'jerk' of the finger, which it is desirable to minimize since the jerk causes undue stress and strains on the cam, introduces vorticities into the flow, and causes vibration and noise.

It is in the scope of the invention wherein the cam comprises single, double or more crescent forms. Hence for example, a crescent form located at the wide radius of the cam avoids a long pressing period where a continuous strong pressure is applied upon the tube. The magnetic forces are pressing the tube. Along this crescent form, the cam is minimally touching the pressing fingers and hence the force for rotating the cam is provided with a minimal measure. Similarly and as another example of one mode of the invention, a crescent form located at the short radius of the cam provides the cam with another possible movement, which is especially useful (i) in tubes with degradated walls; (ii) in pressing mechanism with noticeable production or assembly tolerances; (iii) in using tubes with relatively thin walls (iv) or in cases of insufficient pressing forces. Those cases are characterized by unsealed tubes, whereat leaking is possible.

Figure 2:
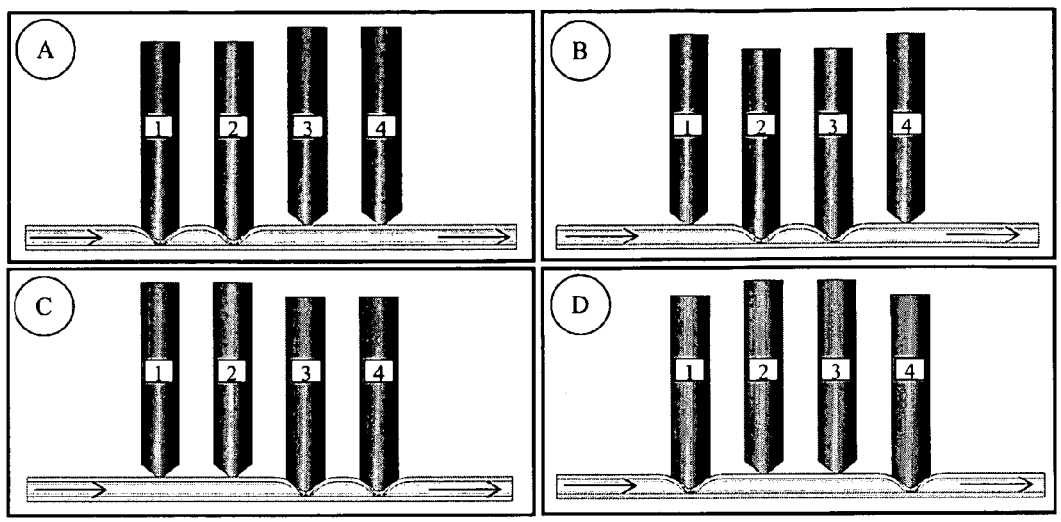
FIG. 2 schematically illustrating the fingers location at each of the four steps of the pumping cycle of a pumping mechanism comprising of four fingers.

Reference is now made to FIG. 2, which illustrates the fingers location at each of the four steps of the pumping cycle of a pumping mechanism comprising of four fingers. FIG. 3 schematically presents the state of each finger at each of the four steps of a single pumping cycle wherein at each step, two fingers are static and two are moving. It is yet according to one embodiment of the invention wherein the rotating cams are designed in a manner that a predefined overlap (e.g., 3%) between adjacent stages is obtained. Hence, one finger is switched from open configuration (tube loosed) to close configuration (tube compressed) only after a short while where an adjacent finger is switched to its close configuration.

Figure 4:
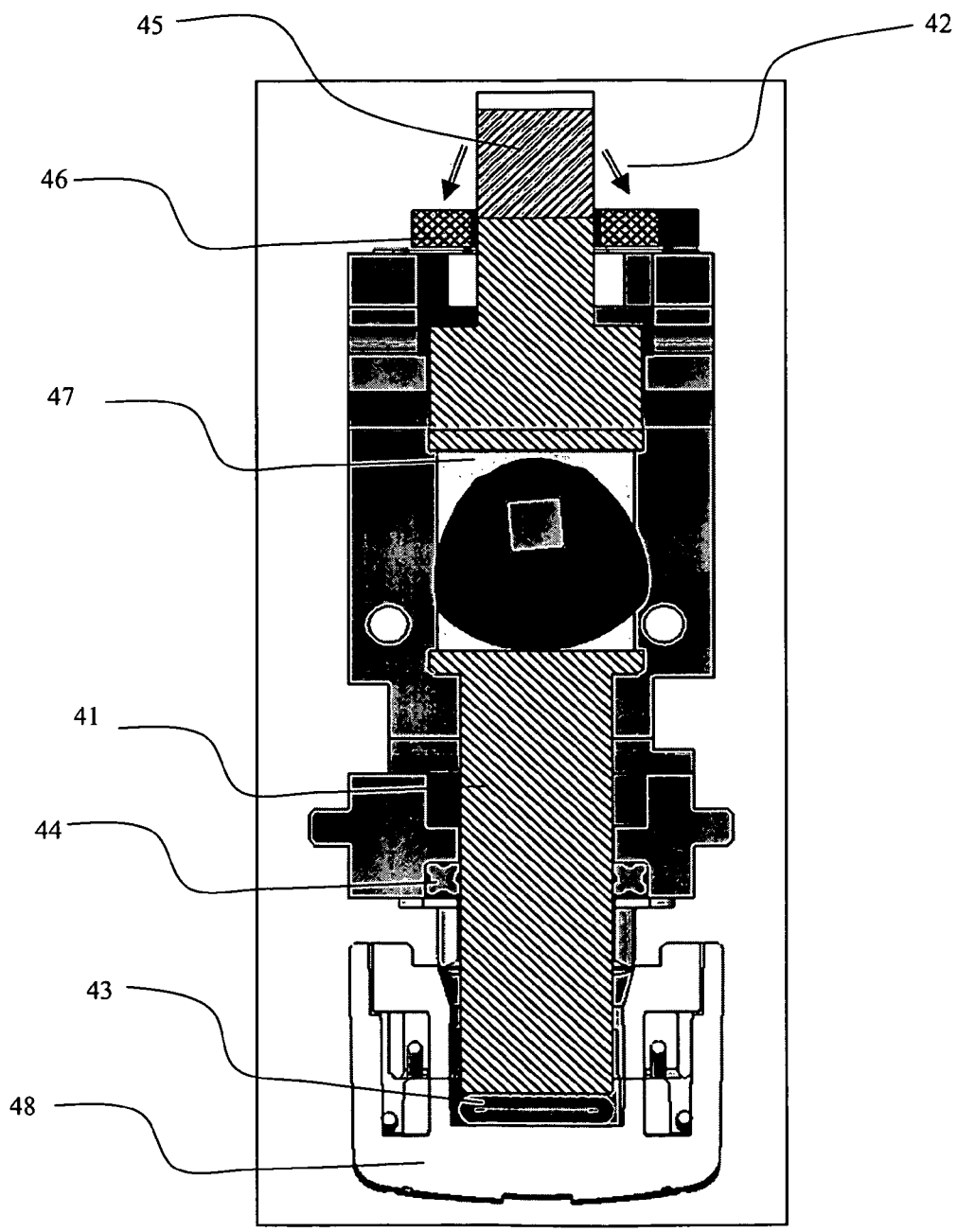
FIG. 4 schematically presents a cross section of the pumping mechanism according to one embodiment of the invention, wherein one portion of the cams is characterized by one crescent form.

Reference is now made to FIG. 4 which schematically presents a cross-section of a pumping mechanism according to one embodiment of the invention. FIG. 4 specifically illustrating one portion of the cams is characterized by one crescent form, adapted to provide pressing of a finger (41), e.g., via a seal (44), by magnetic forces (42) of the balancing magnets in the manner that the magnetic forces are at least slightly stronger, than the oppositely directed elastic forces, provided by the squeezing of the flexible tube by the finger while shutting off the tube (43) against a base (48); by applying the magnetic force, complete tube's shut off is assured, especially in cases of worn out tubes and pumping mechanisms with noticeable tolerances; this pumping mechanism with magnetically balances pressing fingers 41 is provided with preset balancing forces at each point along the path of motion of the moving fingers being of approximately equal magnitude to that of said obstructive forces at this point; such that the parasitic output due to work performed against the obstructive forces is approximately zero and yield is maximized. The pumping mechanism further comprises a magnet (45), ferromagnetic metal (46), and a cam (47a). Here for example, cam 47a is characterized by a single crescent form.

Figure 5:
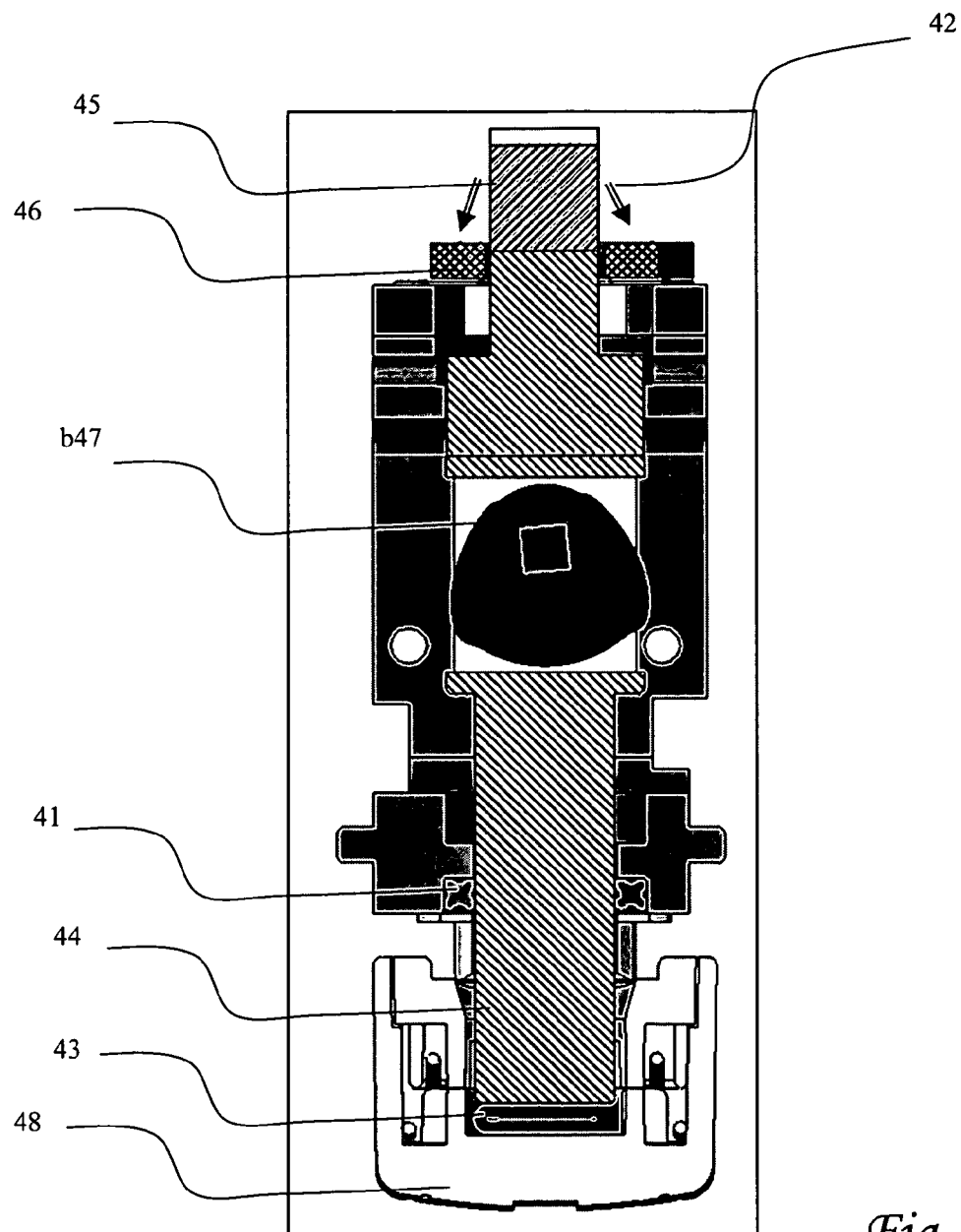
FIG. 5 schematically presents a cross section of the pumping mechanism according to one embodiment of the invention, wherein one portion of the cams is characterized by two crescent forms.
Figure 6:
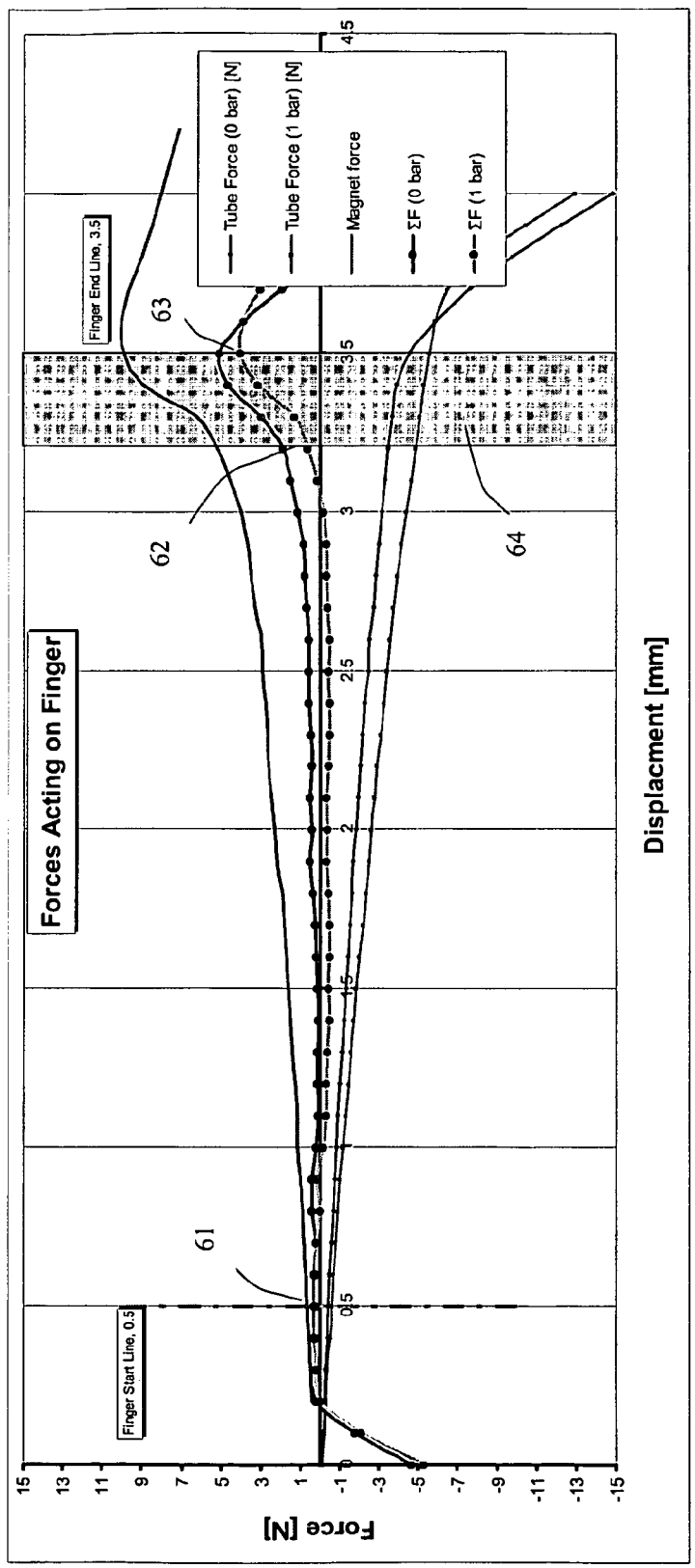
FIG. 6 graphically presents the forces on a single finger applied along a single half pumping cycle.

Reference is now made to FIG. 5, which schematically presents a cross-section of another pumping mechanism according to the present invention, comprises inter alia a magnet 45, ferromagnetic metal 46, and first crescent form of cam 47b which is adapted to provide pressing of finger 41 via a seal (44) by magnetic forces 42 of the balancing magnets in the manner that the magnetic forces are at least slightly stronger, than the oppositely directed elastic forces, provided by the squeezing of flexible tube 43 against a base (48) by the finger while shutting off the tube; by applying said magnetic force, complete tube's shut off is assured; the second crescent form is adapted to provide additional finger movement in the direction of withdrawing the tube, so as to facilitate a more relaxed form of mechanical pressure on the tube walls, especially in wider tubes, tubes of wider walls, and pumping mechanisms with noticeable tolerances; the said more relaxed form of mechanical pressure on the tube enable a prolonged life of the tube and as a consequence a more accurate flow rate throughout the pumping; and, Reference is now made to FIG. 6, which graphically presents the forces on a single finger applied along a single half pumping cycle; wherein point No. 1 symbols the upper point at with the finger tip is reaching through the pumping cycle. At this point almost no force is applied on the tube walls tube walls and the magnet was designed to apply equal small force on the finger so the total force acting between the cam and the finger is zero.

Point 2 denotes for the point in which the finger presses the tube to a flow shut off position; in this point, the magnetic force is greater than the obstructive force applied by the elastic tube so as shut off of the flow is assured at any pressure existing in the tube (up to 1 bar in this sample). At this point the magnet was designed to apply grater force then the force applied by the tube on the finger. This armament facilitates secured shut off of the tube under variant condition with very little total force acting on the finger, i.e. force acting between the cam and the finger is very small leading to decries in wear, energy consumption etc.

Point 3 represents the total force acting on the fingers which is slightly greater due to slightly greater magnetic forces. This design ensures complete shut off (squeeze) of the tube in case where tube walls degradation is presented or in case where a tube with inadequate walls thickness is used. From this point the magnet force acting on the finger decreases to avoid puncturing of the tube.

Point 4 symbols the free movement of the finger to ensure complete shut off of the tube, especially in case of degradation of tube's walls, tolerances in pumping mechanism etc. .SIGMA.F is the total force applied on the finger in the direction of the press, i.e., the magnetic power minus obstructive forces of the elastic tube; the force applied by the cam on the pressing finger approx. equals the aforesaid force plus the forces required to overcome frictions in the pumping system. Point 4 hence describes the point whereat the magnetic forces are stronger than the elastic forces of the tube, such that the tube is effectively sealed.

The invention claimed is:

1. A peristaltic pump comprising:
   a fluid flow channel including a flexible segment;
   at least one effecter including a ferrite member and adapted to intermittently compress the flexible segment within said channel, wherein compression of the flexible segment produces a reactive force;
   at least one electrically triggerable actuator to apply a mechanical force on said effecter; and
   a balancing member to magnetically interact with said ferrite member in said at least one effecter so that a balancing force proportional to the mechanical force on said effecter is produced to substantially counter said reactive force of the flexible segment.

2. The peristaltic pump as in claim 1, wherein the fluid flow channel includes a silicon element.

3. The peristaltic pump as in claim 1, wherein the fluid flow channel has at least a first cross-sectional geometry.

4. The peristaltic pump as in claim 3, wherein the at least first fluid flow channel cross-sectional geometry includes a round cross section.

5. The peristaltic pump as in claim 3, wherein the at least first fluid flow channel cross-sectional geometry includes a rectangular cross section.

6. The peristaltic pump as in claim 3, further comprising an at least second cross-sectional geometry along a length of the channel and said second cross-sectional geometry is different than said first cross-sectional geometry.

7. The peristaltic pump as in claim 1, wherein said at least one effecter is a pressing finger.

8. The peristaltic pump as in claim 1, wherein said ferrite member is a magnetic material and said balancing member includes a metallic material.

9. The peristaltic pump as in claim 1, wherein said ferrite member is a metallic material and said balancing member includes a magnetic material.

10. The peristaltic pump as in claim 1, wherein said ferrite member is a magnetic material and said balancing member includes a magnetic material.

11. The peristaltic pump as in claim 1, wherein said at least one effecter periodically moves relatively to the flexible segment, and said magnetically interacting includes producing a balancing force to substantially counter said reactive force of the flexible segment while the at least one effecter moves.

12. The peristaltic pump as in claim 11, wherein said balancing force substantially counters said reactive force while the at least one effecter moves in forth or backward movement.

13. The peristaltic pump according to claim 1, wherein said balancing member produces a permanent magnetic field.

14. The peristaltic pump according to claim 1, wherein said balancing member is attracted to a magnetic field.

* * * * *